United States Patent
Ouchi

(10) Patent No.: US 6,190,384 B1
(45) Date of Patent: Feb. 20, 2001

(54) ENDOSCOPIC HIGH-FREQUENCY TREATMENT TOOL

(75) Inventor: Teruo Ouchi, Saitama (JP)

(73) Assignee: Asahi Kogaku Kogyo Kabushiki Kaisha, Tokyo (JP)

(*) Notice: Under 35 U.S.C. 154(b), the term of this patent shall be extended for 0 days.

(21) Appl. No.: 09/274,483

(22) Filed: Mar. 23, 1999

(30) Foreign Application Priority Data

Apr. 3, 1998 (JP) .................................................. 10-090517

(51) Int. Cl.[7] .................................................. A61B 18/18
(52) U.S. Cl. .................................. 606/47; 606/46; 606/41
(58) Field of Search .................................... 606/41, 45–50

(56) References Cited

U.S. PATENT DOCUMENTS

| | | | | |
|---|---|---|---|---|
| 5,057,107 | * | 10/1991 | Parins et al. | 606/48 |
| 5,085,659 | * | 2/1992 | Rydell | 606/47 |
| 5,190,541 | * | 3/1993 | Abele et al. | 606/50 |
| 5,197,964 | * | 3/1993 | Parins | 606/48 |
| 5,217,458 | * | 6/1993 | Parins | 606/48 |
| 5,460,629 | * | 10/1995 | Shlain et al. | 606/46 |

* cited by examiner

Primary Examiner—Michael Peffley
(74) Attorney, Agent, or Firm—Greenblum & Bernstein, P.L.C.

(57) ABSTRACT

An endoscopic high-frequency treatment tool includes a flexible sheath, a manipulating wire, a fixed electrode and a moving electrode. The manipulating wire is inserted within the flexible sheath and is movable back and forth along a longitudinal axis thereof. The fixed electrode is connected to a tip of the flexible sheath. The moving electrode is connected to a tip of the manipulating wire, and opposes the fixed electrode to form a predetermined gap therebetween in a direction of the longitudinal axis of the manipulating wire. At least one of the fixing and moving electrodes receives a high-frequency current, and the moving electrode is movable toward and away from the fixed electrode by moving the manipulating wire back and forth.

12 Claims, 5 Drawing Sheets

ENDOSCOPIC HIGH-FREQUENCY TREATMENT TOOL

BACKGROUND OF THE INVENTION

1. Field of the Invention

The present invention relates to an endoscopic high-frequency treatment tool for cauterizing and cutting the stem of a polyp and other tissue masses with a high-frequency current.

2. Description of the Related Art

High-frequency snares are extensively used with endoscopes to remove polyps. The snare includes a flexible sheath in the form of an insulated tube, a conductive manipulating wire passed through the sheath, and a looped wire connected to the tip of the manipulating wire. The operator moves the manipulating wire back and forth along its longitudinal axis, so that the looped wire is constricted or expanded at the tip portion of the flexible sheath.

To remove the polyp with the high-frequency snare, the looped wire is placed around the stem of the polyp. The looped wire is then gradually tightened while a high-frequency current is applied thereto. During this tightening process, there is a gradual cauterizing from the outer surface of the polyp to the inner part.

However, this related high-frequency snare has one serious problem. When the operator pulls the manipulating wire applied with a high-frequency current, the caustic effect of the current starts to cut the outer part of the polyp, but at the same time the constricted looped wire may mechanically tear off a portion of the inner part of the polyp which is not fully cauterized by the high-frequency current, thereby causing bleeding.

SUMMARY OF THE INVENTION

An object, therefore, of the invention is to provide an endoscopic high-frequency treatment tool that can safely cauterize and cut polyps and other tissue masses without potential bleeding.

The present invention attains the stated object by an endoscopic high-frequency treatment tool including a flexible sheath; a manipulating wire inserted within the flexible sheath and being movable back and forth along a longitudinal axis thereof; a fixed electrode connected to a tip of the flexible sheath; and a moving electrode connected to a tip of the manipulating wire, and opposed to the fixed electrode to form a predetermined gap therebetween in a direction of the longitudinal axis of the manipulating wire; wherein at least one of the fixing and moving electrodes receives a high-frequency current, and the moving electrode is movable toward and away from the fixed electrode by moving the manipulating wire back and forth.

The high-frequency current may be applied to the manipulating wire from a base end thereof toward a tip end thereof.

At least one of the fixed and moving electrodes may have a projection formed on a surface that opposes the other electrode.

The fixed and moving electrodes have respective opposing surfaces. At least one of these opposing surfaces may be formed in a substantially rectangular shape having an area that is defined by a length of 2 to 5 mm and a width of 1 to 3 mm.

The fixed electrode may include an opposing portion that faces the moving electrode, and an elongating portion that extends in the longitudinal direction from the tip of the flexible sheath to the opposing portion.

The moving electrode may define a guide groove partially accommodating the elongating portion so as to guide the movement of the moving electrode.

DETAILED DESCRIPTION OF THE INVENTION

Several endoscopic high-frequency treatment tools of the invention are now described with reference to the accompanying drawings.

Figure 1:
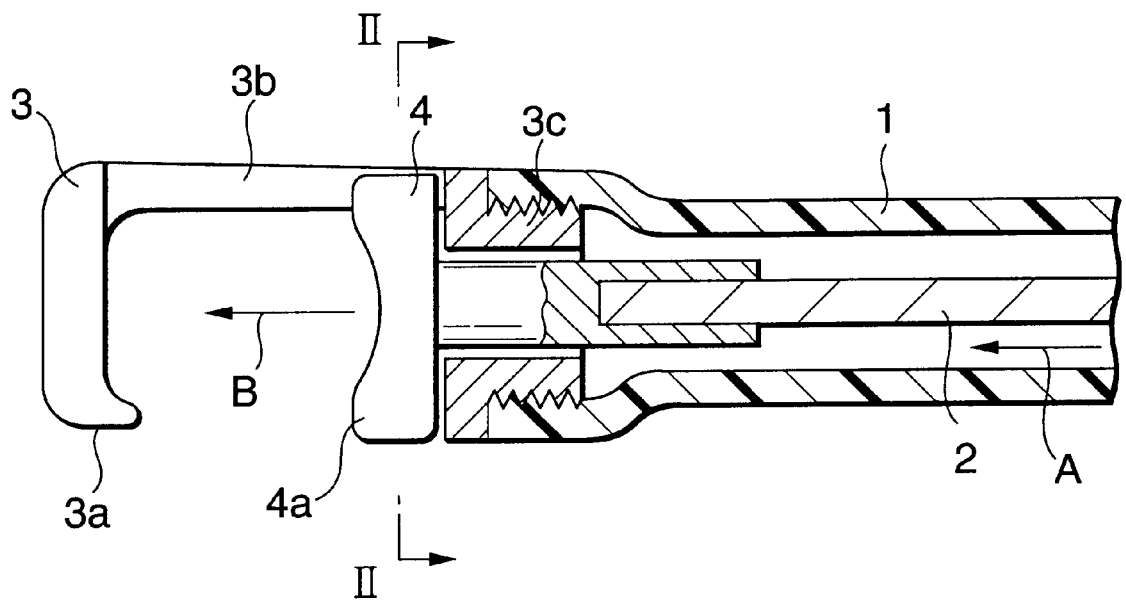
FIG. 1 is a partial sectional view of the tip portion of a first endoscopic high-frequency treatment tool.

FIG. 1 is a partial sectional view of a tip portion of a first endoscopic high-frequency treatment tool.

Reference numeral 1 indicates a flexible sheath that can be inserted into or removed from a treatment tool insertion channel (not shown) through which a treatment tool can be inserted into an endoscope. The flexible sheath 1 is in the form of an electrically insulated tube typically made of a tetrafluoroethylene resin.

A manipulating wire 2 is passed through the entire length of the flexible sheath 1 in such a way that it can move back and forth along the longitudinal axis of the sheath 1. A manipulating section (not shown) is connected to the flexible sheath 1 base end that is closer to the operator who can use the manipulating section to move the wire 2 back and forth.

A fixed electrode 3 made of a conductive metal is securely connected, typically by threading, to the tip of the flexible sheath 1. The fixed electrode 3 is formed in a hook-shape, is projected forward from a connection portion 3c that is connectable with the flexible sheath 1, and has a small projecting end 3a bent in the rearward direction.

A moving electrode 4 also made of a conductive metal is connected, typically by silver brazing, to the tip of the manipulating wire 2. The fixed electrode 3 and the moving electrode 4 are disposed so as to oppose each other with a space therebetween being in the direction of the longitudinal axis of the manipulating wire 2.

If the operator pushes the manipulating wire 2 at the manipulating section side as indicated by arrow A, the moving electrode 4 approaches the fixed electrode 3 as indicated by arrow B. As a result, an opposing end 4a of the moving electrode 4 contacts the projecting end 3a of the fixed electrode 3.

If the operator pulls the manipulating wire 2 at the manipulating section side thereof, the moving electrode 4 is separated from the fixed electrode 3 and returns to the position indicated in FIG. 1. The opposing surfaces of the two electrodes 3 and 4 have an area that is defined by a length of about 2 to 5 mm and a width of about 1 to 3 mm.

The manipulating section (not shown) has a known connection terminal for connecting the manipulating wire 2 to a high-frequency power supply, and a high-frequency current can be applied at a desired time to the moving electrode 4 via the manipulating wire 2.

Figure 2:
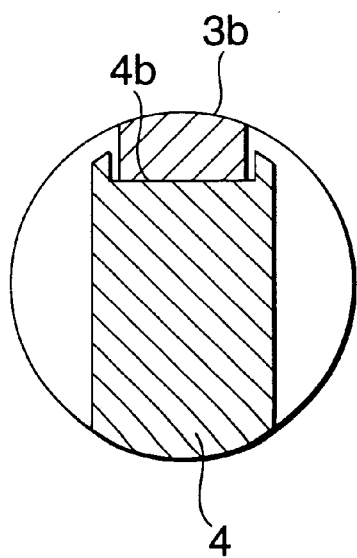
FIG. 2 is a sectional view taken along the line II—II of FIG. 1 showing the first endoscopic high-frequency treatment tool.

As shown in FIG. 2, a groove 4b of a specified width is formed on one side of the moving electrode 4 so as to be flat along the direction of the longitudinal axis of the wire 2. An intermediate portion 3b of the fixed electrode 3 formed in a hook-shape engages with the groove 4b in a rail-like manner. With this arrangement, the moving electrode 4 does not rotate relative to the fixed electrode 3, and does not shake while it moves back and forth.

Figure 3:
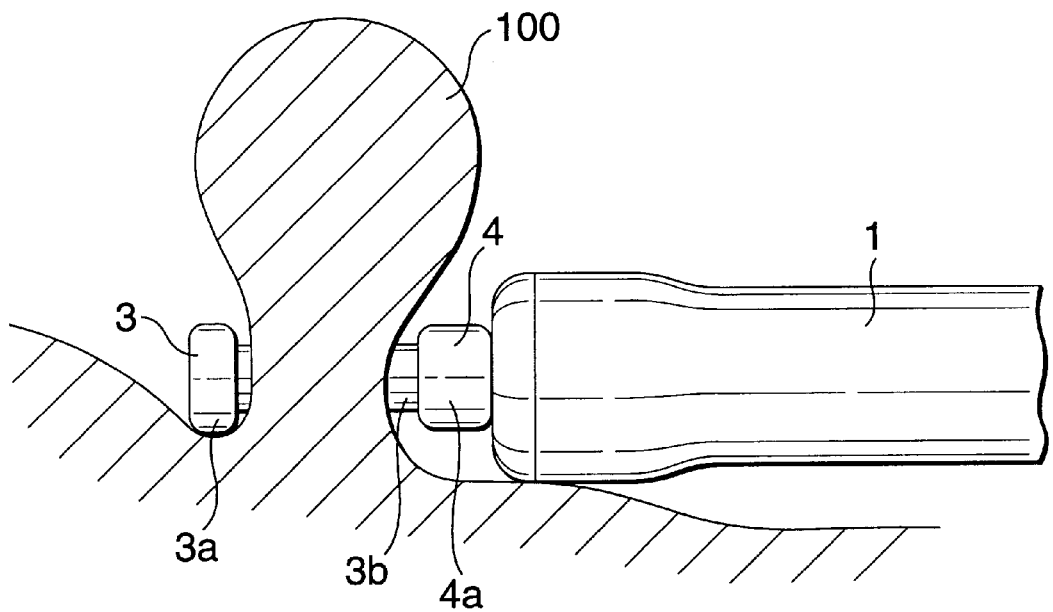
FIG. 3 is a side view of the tip portion of the first endoscopic high-frequency treatment tool in action.

Since the fixed electrode 3 and the moving electrode 4 are in contact at all times, a high-frequency current applied to the moving electrode 4 is also transmitted to the fixed electrode 3. In this treatment tool, the fixed electrode 3 and the moving electrode 4 are formed to have substantially the same width, as shown in FIG. 3.

To cut a polyp with the aid of an endoscope by using the first endoscopic high-frequency treatment tool, the following general procedure is followed.

First, the flexible sheath 1 is inserted into the treatment tool insertion channel. Then, as shown in FIG. 3, the fixed electrode 3 and the moving electrode 4 are separated to the fullest extent and the stem of the polyp 100 is placed between the two electrodes.

Figure 4:
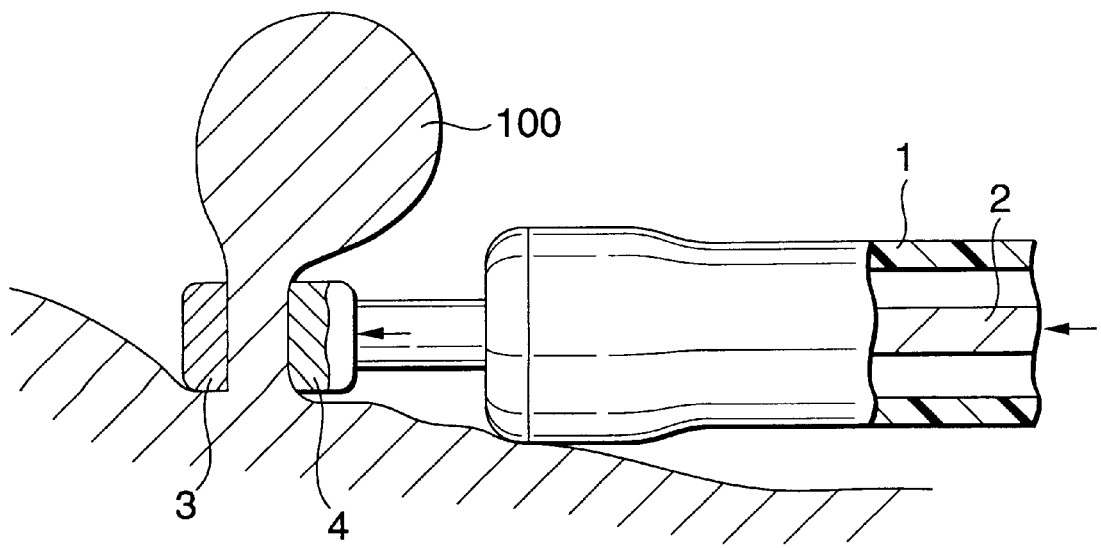
FIG. 4 shows a partial side sectional view of the tip portion of the first endoscopic high-frequency treatment tool in action.

Thereafter, a high-frequency current is applied while an operator lightly pushes the manipulating wire 2. Then, as shown in FIG. 4, the stem of the polyp 100 is pinched between the two electrodes, and the tissue of the polyp in contact with the electrodes is cauterized by the high-frequency current, so that the polyp 100 is cut off. Since the electrodes do not apply a sufficient mechanical force to sever the stem of the polyp 100, the polyp 100 is not mechanically cut, and hence no bleeding will occur.

Figure 5:
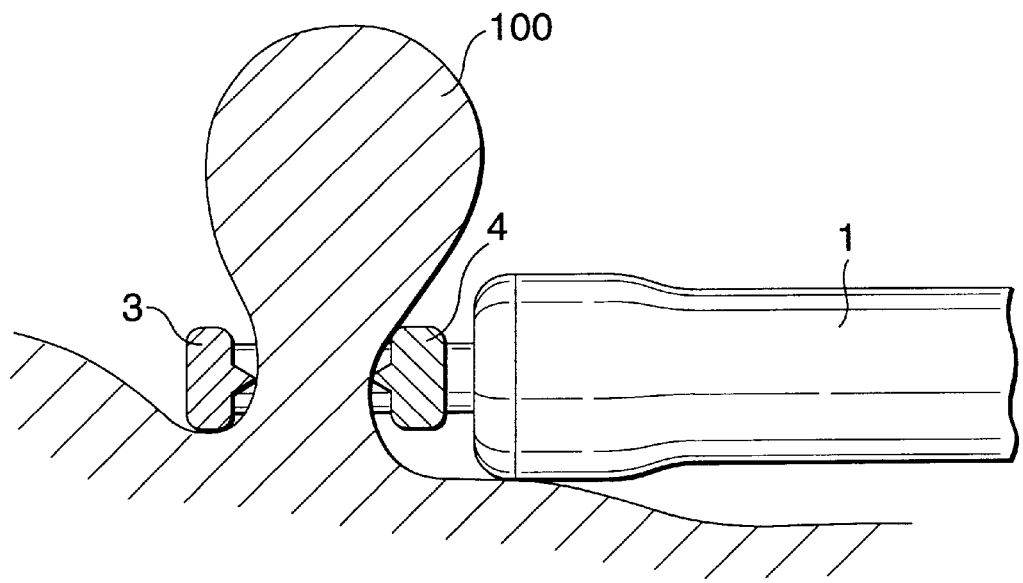
FIG. 5 shows a partial longitudinal section of the tip portion of a second endoscopic high-frequency treatment tool in action.

FIG. 5 shows a partial longitudinal section of a second endoscopic high-frequency treatment tool in action. A projection having a triangular shape is formed on each of the opposing surfaces of the electrodes 3 and 4. With this structure, the electrodes contact the mucosal surface in only a small area, and the density of the applied high-frequency current is greatly increased to thereby enhance the efficiency of the high-frequency electrocautery.

Figure 6:
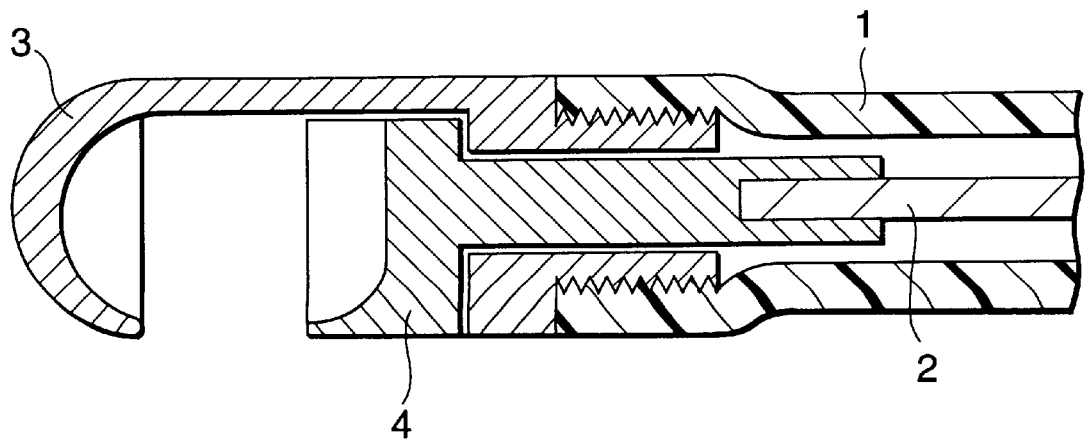
FIG. 6 is a sectional view of the tip portion of a third endoscopic high-frequency treatment tool.
Figure 7:
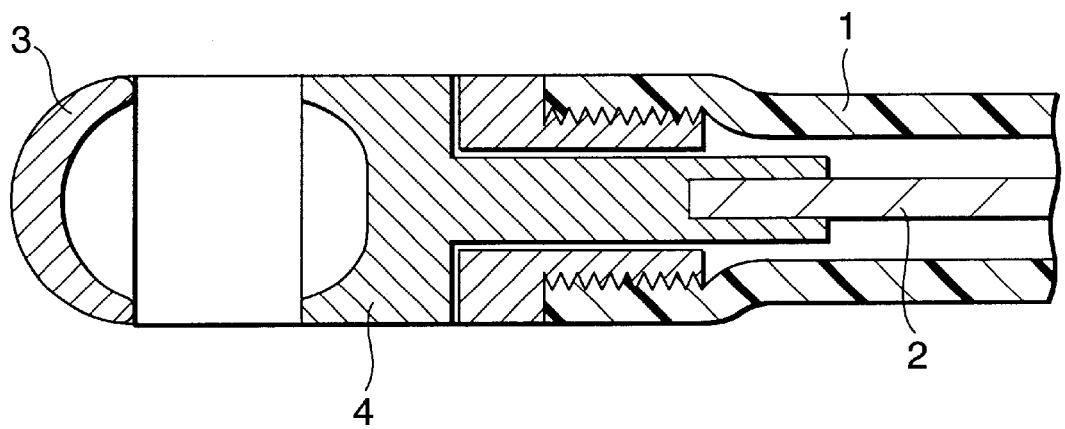
FIG. 7 is another sectional view of the tip portion of the third endoscopic high-frequency treatment tool, taken from a different angle.

FIG. 6 is a sectional view of the tip portion of a third endoscopic high-frequency treatment tool. FIG. 7 is another sectional view of the same tip portion when viewed from the bottom side of the section shown in FIG. 6. In this treatment tool, both the fixed electrode 3 and the moving electrode 4 are formed in a substantially hemispherical cup shape.

Figure 8:
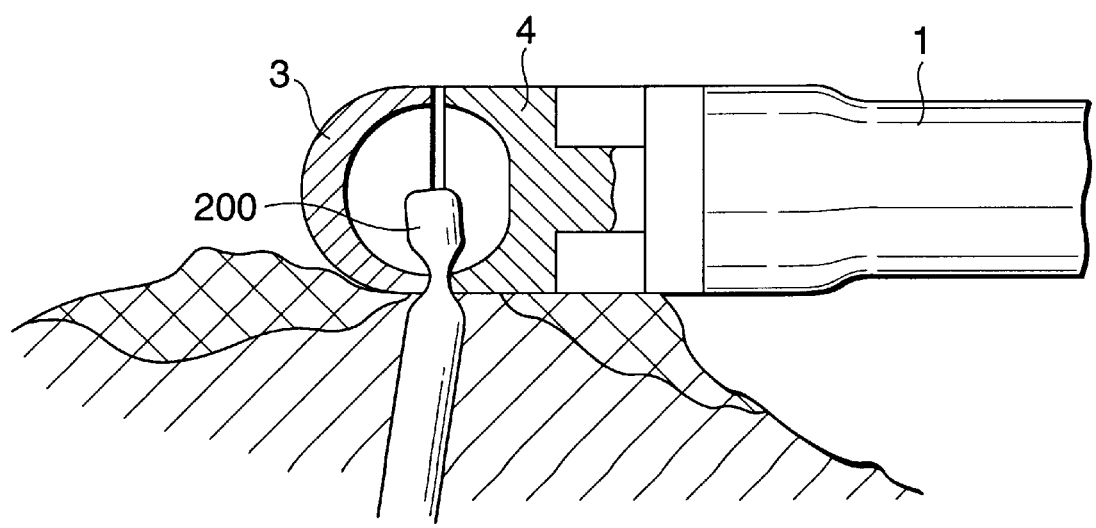
FIG. 8 is a partial sectional view of the tip portion of the third endoscopic high-frequency treatment tool in action.

With this design, as shown in FIG. 8, the neighborhood of a cut end of a thick blood vessel 200 exposed on the mucosal surface after removing the polyp can be pinched between the electrodes 3 and 4, cauterized and cut off to prevent bleeding.

Figure 9:
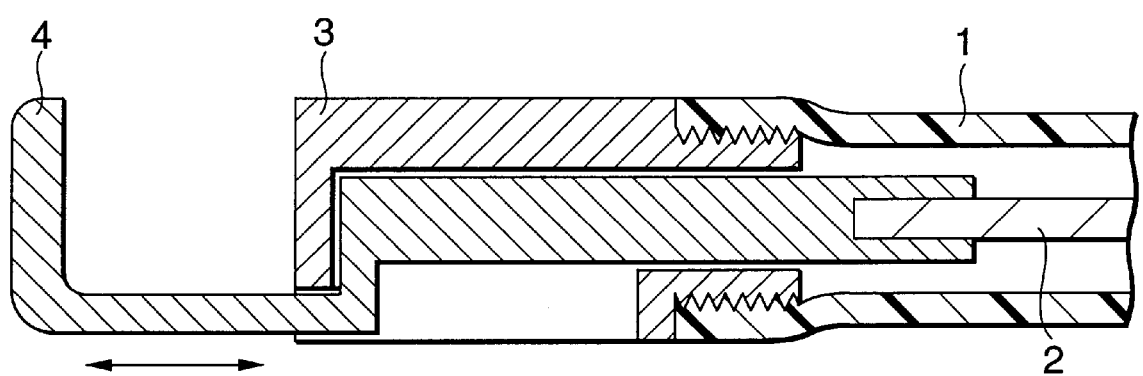
FIG. 9 is a sectional view of the tip portion of a fourth endoscopic high-frequency treatment tool.

FIG. 9 shows the tip portion of a fourth endoscopic high-frequency treatment tool. In this treatment tool, the relative positions of the fixed electrode 3 and the moving electrode 4 are reversed from those of the first endoscopic high-frequency treatment tool such that the moving electrode 4 connected to the manipulating wire 2 is positioned ahead of the fixed electrode 3.

Thus, the endoscopic high-frequency treatment tool of the invention permits various modifications as long as a high-frequency current can be applied to either the fixed electrode 3 or the moving electrode 4 or both. It should be noted that a high-frequency current may be applied via a conductive member other than the manipulating wire 2.

According to the invention, the fixed electrode connected to the tip of the flexible sheath and the moving electrode connected to the tip of the manipulating wire are disposed so as to oppose each other. A space is formed between the fixed electrode and the moving electrode in the direction of the longitudinal axis of the manipulating wire. The operator manipulates the manipulating wire back and forth to thereby cause the moving electrode to depart from or approach the fixed electrode. When the stem of a polyp or other tissue mass is pinched between the two electrodes and supplied with a high-frequency current, the polyp or other tissue mass can be cauterized and cut off without mechanical force. In this way, the polyp or other tissue mass can be removed in a very safe manner without potential bleeding.

The entire disclosure of each and every foreign patent application from which the benefit of foreign priority has been claimed in the present application is incorporated herein by reference, as if fully set forth.

While only certain embodiments of the invention have been specifically described herein, it will be apparent that numerous modifications may be made thereto without departing from the spirit and scope of the invention.

What is claimed is:

1. An endoscopic monopolar high-frequency treatment tool comprising:
   a flexible sheath;
   a manipulating wire extending through and within said flexible sheath and being movable back and forth along a longitudinal axis thereof;
   a fixed electrode connected to a tip of said flexible sheath; and
   a moving electrode connected to a tip of said manipulating wire, and opposed to said fixed electrode to form a gap therebetween in a direction of the longitudinal axis of said manipulating wire;
   wherein at least one of said fixed and moving electrodes receives a high-frequency current, and said moving electrode is movable toward and away from said fixed electrode by moving said manipulating wire said moving electrode and said fixed electrode being electrically coupled to each other throughout a range of movement of said moving electrode.

2. The endoscopic high-frequency treatment tool according to claim 1, wherein the high-frequency current is applied to said manipulating wire from a base end thereof toward a tip end thereof.

3. The endoscopic high-frequency treatment tool according to claim 1, wherein at least one of said fixed and moving electrodes has a projection formed on a surface opposing the other electrode.

4. The endoscopic high-frequency treatment tool according to claim 1, wherein said fixed and moving electrodes have respective opposing surfaces, and at least one of said opposing surfaces is formed in a substantially rectangular shape having an area that is defined by a length of 2 to 5 mm and a width of 1 to 3 mm.

5. The endoscopic high-frequency treatment tool according to claim 1, wherein said fixed electrode includes an opposing portion facing said moving electrode, and an elongating portion extending in the longitudinal direction from the tip of said flexible sheath to the opposing portion.

6. The endoscopic high-frequency treatment tool according to claim 5, wherein said moving electrode defines a guide groove partially accommodating the elongating portion so as to guide the movement of said moving electrode.

7. An endoscopic high-frequency treatment tool comprising:

a flexible sheath;

a manipulating wire extending through and within said flexible sheath and being movable back and forth along a longitudinal axis of said flexible sheath;

a source of high-frequency current;

a fixed electrode connected to a tip of said flexible sheath;

a movable electrode connected to a tip of said manipulating wire, and opposed to said fixed electrode to form a gap between said fixed electrode and said moving electrode, in a direction of the longitudinal axis of said manipulating wire, high-frequency current from said source being conducted from one of said fixed and movable electrodes to the other of said fixed and movable electrodes; and said movable electrode being movable toward and away from said fixed electrode by movement of said manipulating wire.

8. The endoscopic high-frequency treatment tool according to claim 7, wherein the high-frequency current is applied to said manipulating wire from a base end of said wire toward a tip end of said manipulating wire.

9. The endoscopic high-frequency treatment tool according to claim 7, wherein at least one of said fixed electrode and said movable electrode has a projection formed on a surface opposite the other of said fixed electrode and said movable electrode.

10. The endoscopic high-frequency treatment tool according to claim 7, wherein said fixed electrode and said movable electrode each have respective opposing surfaces, and at least one of said opposing surfaces is formed in a substantially rectangular shape having an area that is defined by a length of 2 to 5 mm and a width of 1 to 3 mm.

11. The endoscopic high-frequency treatment tool according to claim 7, wherein said fixed electrode includes an opposing portion facing said movable electrode, and an elongation portion extending in the longitudinal direction from the tip of said flexible sheath to the opposing portion.

12. The endoscopic high-frequency treatment tool according to claim 11, wherein said movable electrode defines a guide groove partially accommodating the elongation portion so as to guide movement of said movable electrode.

* * * * *